United States Patent [19]

Young

[11] Patent Number: 4,790,328

[45] Date of Patent: Dec. 13, 1988

[54] DEVICE FOR DIAGNOSIS AND TREATMENT OF URINARY INCONTINENCE

[76] Inventor: David E. Young, Bowlers Piece, 16 Couching Street, Watlington, Oxon, England, OX9 5QQ

[21] Appl. No.: 97,636

[22] Filed: Sep. 16, 1987

[30] Foreign Application Priority Data

Sep. 24, 1986 [GB] United Kingdom ............... 8623020

[51] Int. Cl.$^4$ ............................................. A61B 10/00
[52] U.S. Cl. .................................... 128/748; 128/674; 128/733
[58] Field of Search ....................... 128/748, 672–673, 128/675, 774, 778, DIG. 25, 733

[56] References Cited

U.S. PATENT DOCUMENTS

| 4,191,196 | 3/1980 | Bradley et al. | 128/748 X |
| 4,217,911 | 8/1980 | Layton | 128/748 |
| 4,233,991 | 11/1980 | Bradley et al. | 128/748 X |
| 4,265,243 | 5/1981 | Taylor | 128/760 X |
| 4,621,647 | 11/1986 | Loveland | 128/748 |

FOREIGN PATENT DOCUMENTS

0039467A2 11/1981 European Pat. Off. .
2151139A 7/1985 United Kingdom .

OTHER PUBLICATIONS

Glen et al.; "Continuous Flow Cystometry and Urethral Pressure Profile Measurement with Monitored Intracranial Pressure"; Urol. Res. 1, 1973, pp. 97–100.
Willington, F. L., Therapeutic Distension for Detrusor Instability in the Elderly, Proceedings of International Continence Society, pp. 13–17, Aug.-Sep. 1978.
Cardozo, L., et al., Biofeedback in the Treatment of Detrusor Instability, Brit. Journal of Urology, vol. 50, pp. 250–254 (1978).
Thomas, T. M., et al, Prevalence of Urinary Incontinence, Brit. Medical Journal, vol. 281, pp. 1243–1245 (1980).
Holm, H. H., et al, Disposable Apparatus for Closed Bladder Tidal Drainage, Journal of Urology, vol. 104, pp. 753–754 (1970).
Bajpai, M., et al, Comparison of Cystomat and Multichannel Cystometry in the Diagnosis of Bladder Instability, Proceedings of International Continence Society, pp. 203–204, Sep. 1982.

Primary Examiner—Edward M. Coven
Assistant Examiner—Angela D. Sykes
Attorney, Agent, or Firm—Tilton, Fallon, Lungmus

[57] ABSTRACT

A cystometric device for use in the diagnosis and treatment of urinary incontinence caused by detrusor instability. The device includes an opaque, vertically-elongated, rigid body of substantially uniform cross section throughout its length having a vertically-extending channel along its front face and a pair of similar channels along its rear face. The channels are of incomplete circular cross section and receive flexible transparent tubing utilized in the circuitry of the cystometric system. Because of the configuration and opacity of the body, the tubing retained in the front channel can be observed from the front of the device while the tubing received in the rear channels is concealed from view.

6 Claims, 1 Drawing Sheet

U.S. Patent        Dec. 13, 1988        4,790,328
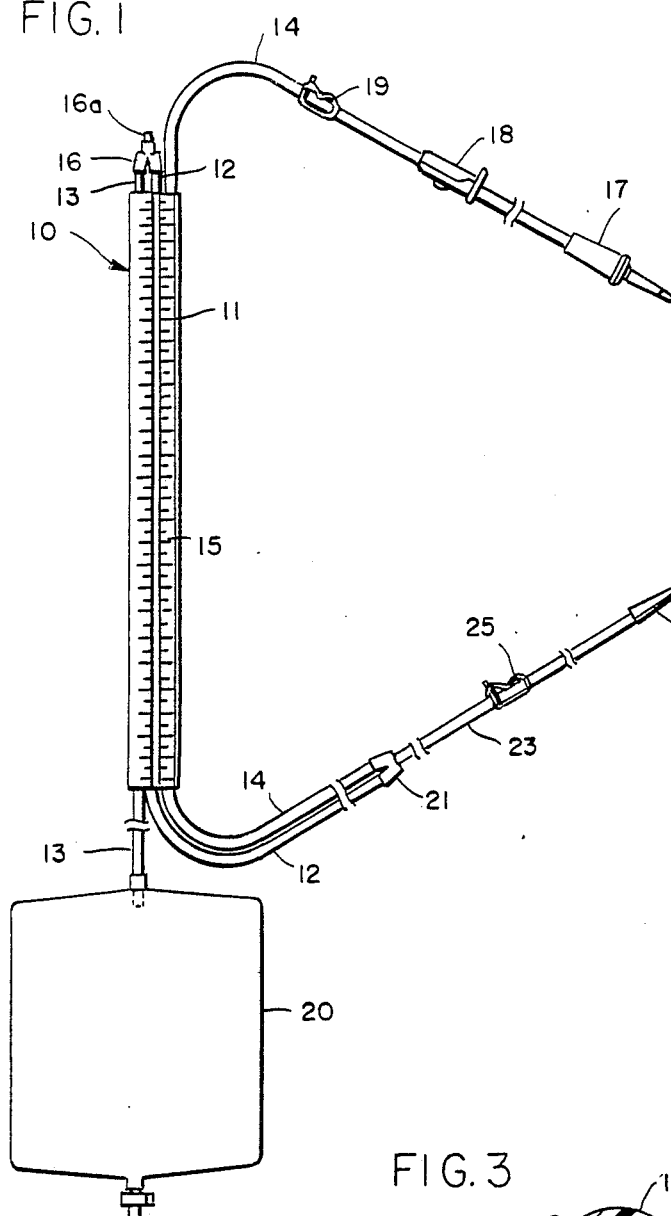
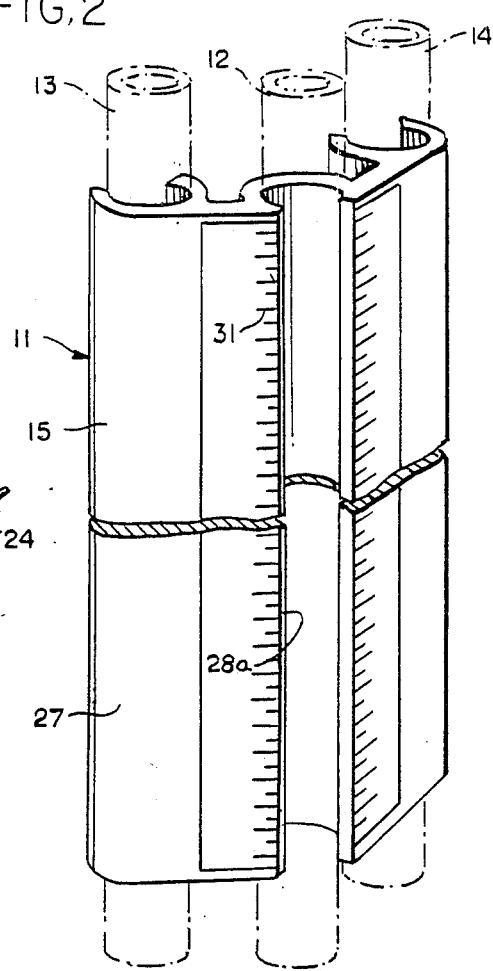
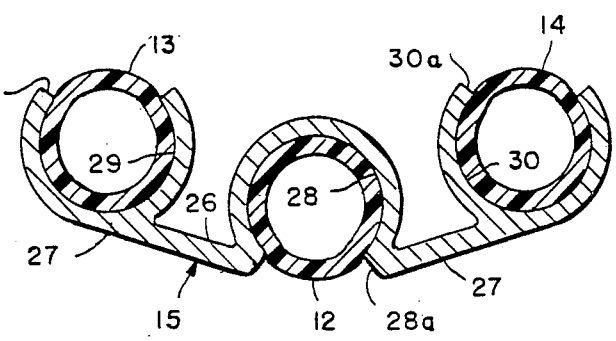
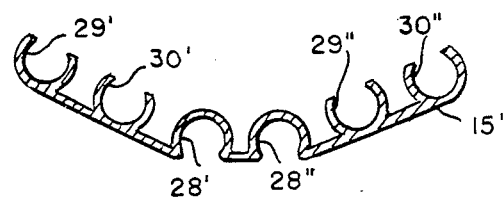

DEVICE FOR DIAGNOSIS AND TREATMENT OF URINARY INCONTINENCE

BACKGROUND AND SUMMARY

Urinary incontinence is extremely widespread in the developed countries. Thomas, Plymat, Blannin and Meade, writing in the British Medical Journal in November 1980, stated that in their large scale survey, 8.5% of women and 1.6% of men in the age group 15-64 are regularly incontinent and that in the 65 and over age group the incidence rises to 11.6% in women and 6.9% in men. This study in London and South Wales suggests that in the United Kingdom there may be nearly 2.5 million regularly incontinent of urine and nearly twice as many who are occasionally incontinent. There seems to be no grounds for believing that the incidence is significantly less in other major European countries and the United States.

It is now well understood that urinary incontinence in women is due to two main causes which may occur alone or together. Genuine Stress Incontinence (GSI) is the accepted International Continence Society term for incontinence caused by incompetence or weakness of the bladder neck and proximal urethra in response to stress events such as coughing, laughing or vigorous postural change. The second cause, Detrusor Instability (DI) involves unstable and involuntary contractions of the bladder; these may also be initiated by a stress event and commonly give rise to symptoms of urge, frequency, and nocturia. Since the causes for the two types of incontinence are different, the treatments are not the same. For example, for GSI, treatment may be by physiotherapy if the condition is mild, but more usually there is recourse to surgery. For DI, surgery has generally proved unsuccessful.

DI is detected by cystometry. In practice, cystometry is generally carried out using equipment which measures the pressure response of the bladder to filling at a constant monitored rate.

Conventional cystometric equipment has generally been expensive and sophisticated. In addition to recording pressure inside the bladder, it also records the intraabdominal pressure (that pressure within the abdomen due to the presence and movement of the viscera). The pressure due to detrusor contraction is measured by the use of a catheter in the bladder, that due to intra-abdominal pressure by a balloon on a catheter in the rectum. Both of these pressures are typically displayed on pen recorder charts and an additional channel electronically subtracts the visceral pressure from the apparent bladder pressure to reveal the component which is solely due to contractions of the detrusor muscle.

Simpler alternatives are possible. In 1982, Bajpai, Sutherst and Brown reported to the 12th Annual Meeting of the International Continence Society their results comparing a simple single-channel cystometer with sophisticated multi-channel equipment on a single-blind crossover basis. They found agreement in findings between the two methods in more than 90% of cases and there were no false negatives. This latter point is important since a negative result on cystometry in the presence of incontinent symptoms would suggest a diagnosis of GSI and, as indicated, that could lead to an erroneous decision to undertake surgery.

With regard to the treatment of DI, probably the most encouraging work has been carried by Willington and Cardozo et al in the United Kingdom. That work involved mild therapeutic distension of the bladder in what has been referred to as the "biofeedback principle." Unlike other more complicated methods of treatment, the Willington et al treatment is simple, innocuous, effective, repeatable, and lacks adverse side effects.

Willington employed an apparatus sold commercially under the name "Cystomat" disclosed by Holm and Egleblad in The Journal of Urology in 1970. The authors describe a siphon device for tidal drainage of the bladder although they do not appear to have contemplated use of the device either as a cystometer or for biofeedback treatment of DI. The Cystomat does, however, feature a tubing arrangement which makes such applications possible.

Published British application No. 2 151 139A (D. E. Young) discloses a cystometric apparatus in which three rigid tubes are clipped together to provide a device for use in a system for diagnosing and treating urinary incontinence caused by detrusor instability. Two of the rigid tubes are formed of opaque material; the third is transparent and functions as an observation tube. The upper ends of the tubes are connected by a headpiece with a vented channel between the observation tube and one of the opaque tubes. The device is attached to a source of sterile fluid and to a patient's bladder by means of flexible tubing and a catheter, and a bag or other collecting receptacle also communicates with the device. The apparatus, although notably effective in diagnosing and treating DI, requires the use of specialized rigid transparent and opaque tubing. Twisting and other stresses imposed on the tubing during handling and sterilization procedures may weaken or disrupt the connections between the tubes and the members that hold them together. Such stresses may be particularly severe because of the substantial length of the rigid tubes and their relatively small diameter. Rigidity of the tubes is important in the operation of the system, at which time the tubes must be vertically oriented, but such rigidity may present a problem of breakage which, should it occur, would disrupt the integrity and sterility of the system. The rigid tubes must also have certain of their ends coupled to flexible tubulature that communicates with a fluid source, a catheter, and a collection vessel, and such junctions between rigid and flexible tubing always present risks of possible disconnection.

Accordingly, an important aspect of this invention is to provide a device for diagnosing and treating urinary incontinence due to detrusor instability which achieves all of the advantages of prior devices without the disadvantages inherent in earlier systems. The components of this device may be easily assembled, either by a manufacturer or user, utilizing flexible, transparent tubing of the type commonly used in medical applications. The sections of tubing that function as components of the measuring device are securely held in straight, parallel condition by a rigid, opaque body component. Because of the orientation of the tubes and the configuration and opacity of the body, a user may readily observe the fluid level in the transparent observation tube while, at the same time, the parallel sections of the other transparent tubes are concealed from view.

Briefly, the cystometric device comprises a straight, vertically-elongated body formed of rigid and opaque material (or a transparent material subsequently treated to make it opaque) that may conveniently be formed by extrusion. The body is of substantially uniform cross section throughout its length and has a front face and a rear face. A vertical front channel extends along the length of the front face and a pair of rear channels extend along the length of the rear face. In a preferred embodiment, the body is essentially triangular in cross section with the front channel extending along the apex and the rear channels extending along the base of the triangle.

The plural channels may be identical in size and configuration, each being of incomplete circular shape, that is, of generally C-shaped cross sectional configuration. Each channel therefore has a longitudinal opening that communicates with the interior of the channel, with the longitudinal opening of the front channel facing in a direction opposite from the longitudinal openings of the rear channels. The width of each longitudinal opening is sufficient to permit the lateral insertion and removal of a resilient tube into and out of each of the channels and, ideally, the diameter of each channel is slightly smaller than the tube's outside diameter so that the recovery forces exerted by the tube provide a secure frictional interfit between the parts.

Other features, advantages, and objects will appear from the drawings and detailed description of preferred embodiments.

DRAWINGS

FIG. 1 is a somewhat schematic elevational view illustrating a system incorporating the elements of this invention.

FIG. 2 is an enlarged fragmentary perspective view showing the body component of this invention and illustrating in phantom the tubes supportable thereby.

FIG. 3 is a greatly enlarged cross sectional view of the body and tube components.

FIG. 4 is an enlarged sectional view depicting another embodiment of this invention.

DETAILED DESCRIPTION OF PREFERRED EMBODIMENTS

FIG. 1 illustrates a complete cystometric apparatus 10 that, except for important differences described in detail below, bears structural and functional similarities to the apparatus disclosed in published British patent application GB No. 2 151 139A. The common features will therefore be discussed only briefly herein, and reference may be had to such published application for a more detailed discussion of the apparatus and its method of operation.

The apparatus includes a fluid-measuring section 11 in which a plurality of straight, parallel tubes 12-14 are maintained in vertical position by holding means 15. A first tube 12, which is an observation tube, communicates at its upper end with one tubular arm of a three-way connector 16 which may conveniently take the form of an inverted Y-connector. A second tube 13 has its upper end communicating with a second tubular arm of the connector 16 with the third and uppermost arm of that connector being fitted with a simple air bleed element 16a. That element may take the form of a cylindrical blanking piece having a fine axial hole extending through it.

The third tube 14 extends well beyond the upper end of the holding means 15 and is fitted at its upper end with a suitable connector for joining the tube to a fluid source. As the fluid will be intended for infusion into the bladder, it is safe and convenient to use a standard combined drip chamber and trocar component 17 which may be readily attached to a bag or other container of sterile saline (not shown). Below (or proximal to) the drip chamber is fitted a roller clamp 18 and a snap clamp 19, both of which constitute means for controlling flow through the line. The roller clamp 18 regulates flow rate, whereas clamp 19 has only two positions providing for a flow or no-flow condition. Together, the two clamps allow flow rate to be set to the correct level so that the fluid feed to the bladder can then be switched on and off at will without requiring readjustment of the flow rate on each such occasion.

The lower end of the second tube continues well beyond holding means 15 (a convenient length being about 100 cm.) and communicates at its end with a drainage container 20. The container may take the form of a urine drainage bag (as shown) or any other suitable receiver or receptacle. The first and third tubes 12 and 14 also extend well below the lower end of the holding means, preferably a distance within the range of about 100 to 200 cm., and are connected at their ends to adjacent arms of a Y-connector 21. The third arm of that connector is connected to a length of flexible tubing 23 which is terminated with a standard catheter connector 24. A shut-off clamp 25 providing for either a flow or no-flow condition is carried by tubing 23.

The tube holding means of this invention takes the form of a straight, vertically-elongated body 15 of substantially uniform cross section throughout its full length. The body may be formed of any suitable rigid material; while a rigid plastic such as polyvinyl chloride has been found effective, other relatively rigid plastic materials, or other materials such as metal or even wood, may be used. Plastics or metal are preferred because the body may be conveniently formed by extrusion. Whatever material is selected, the body 15 must be opaque, either because of the opacity of the material itself or because of a subsequent coating or other surface treatment.

In the embodiment depicted in FIGS. 1-3, body 15 is generally triangular or V-shaped in cross sectional configuration and has a rear surface 26 and a front surface 27. A longitudinal first or front channel 28 extends along the apical region of the body and includes a longitudinal opening 28a of lesser width than the diameter of the channel. The inner surface of the channel has the configuration of an incomplete circle, or is generally C-shaped, when viewed in cross sectional outline.

The body 15 also includes a pair of rear channels 29 and 30 of substantially the same dimensions as front channel 27. Thus, each of the rear channels has a longitudinal opening or gap 29a and 30a, respectively.

An important fact is that the front and rear channels of the body face in opposite directions. In the illustration given, the longitudinal openings of the rear channels 29 and 30 face approximately 180° away from the direction of the longitudinal opening of the front channel 28. While the difference in direction may be less than 180°, it is believed significant that the channels and their openings are arranged so that a user viewing a tube in the front channel 28 through the longitudinal opening 28a has no direct view of the tubular sections retained in rear channels 29 and 30.

While the construction of body 15 does not preclude the use of rigid tubing sections within channels 28-30, the use of flexible, resilient tubing is particularly advantageous. Such a construction allows an uninterrupted length of tubing 12 to extend from connector 16 to connector 21, an uninterrupted length of tubing 13 from connector 16 to bag 20, and an uninterrupted length of tubing 14 from trocar 17 to connector 21. Because of the resilience of the tubing, stretches of such tubing may be laterally inserted into the channels 28-30 where they are then retained because of the recovery forces exerted by the tubing and the reduced dimensions of the longitudinal openings 28a-30a through which they are introduced. Such retention may be enhanced if as indicated in FIG. 3, the diameter of each channel is slightly smaller than the outside diameter of the tube received therein when that tube is in its undeformed or uncompressed state. Such a relationship means that the sections of tubes 12-14 retained within channels 28-30 do not entirely recover their original shape but bulge slightly into the longitudinal openings for those channels. The outward force exerted by the tubes therefore helps retain them securely in position.

Tube 12, or at least that section of the tube extending through the elongated body 15, must be transparent, whereas tubing 13 and 14 may or may not be transparent. The availability of transparent flexible tubing formed of polyvinyl chloride or other suitable plastic material, and the fact that the sections of tubing 13 and 14 retained in channels 29 and 30 are concealed from the view of a person looking directly at the front of the body and at tube 12 retained within channel 28, makes the use of similar transparent material for all tubes both practical and desirable.

Suitable indicia in the form of the scale markings 31 and numerical indicia (not shown) may be imprinted on the front face 27 of the body adjacent longitudinal opening 28a or, alternatively, may be applied to a tape or label affixed to such surface. A user may therefore readily determine the fluid level within the transparent tube 12 as part of the diagnostic or treatment procedure.

The length of body 15 depends in part on whether the device is to be used for diagnosis or treatment. In a system intended only for treatment, the body may be as short as 20 cm. for use with tubes having an outside diameter of about 7 mm. However, if diagnostic use is contemplated, a body of substantially greater length, for example, 80 cm. or more (for tubing of the same outside diameter) is preferred.

Some authorities contend that diagnostic cystometry cannot adequately differentiate between a true bladder contraction and a rise in intra-abdominal pressure unless there is a rectal as well as a bladder channel. FIG. 4 illustrates how the tube-holding means may be modified to provide an observation tube for bladder flow and one for rectal flow. Thus, body 15' provides front channels 28' and 28" for receiving transparent observation tubes (not shown) for bladder flow and rectal flow, as well as channels 29' and 30', and 29" and 30", for completing the respective circuits. Except for dimensional and configurational changes required for providing an increased number of channels, the embodiment of FIG. 4 is essentially the same in construction and operation as the first embodiment.

While in the foregoing I have disclosed embodiments of the invention in considerable detail for purposes of illustration, it will be understood by those skilled in the art that many of these details may be varied without departing from the spirit and scope of the invention.

I claim:

1. A cystometric device for diagnosing and treating urinary incontinence, comprising a straight, vertically-elongated body of substantially uniform cross section throughout its length having a front face and a rear face; a vertical front channel extending along the length of said front face and a pair of vertical rear channels extending the length of said rear face; at least said front channel being of C-shaped horizontal cross-sectional outline and having a forwardly-directed longitudinal opening of a width smaller than the maximum cross-sectional dimension of such channel; said body being opaque and concealing said rear channels from the view of a user facing the longitudinal opening of said front channel.

2. The device of claim 1 in which all of said channels are of said C-shaped cross-sectional outline and have longitudinal openings therealong.

3. The device of claims 1 or 2 in which tubing is received within each of said channels; at least said tubing in said front channel being formed of transparent material.

4. The device of claim 3 in which said tubing in at least said front channel is resilient and flexible and has an outside diameter in a relaxed state slightly larger than the inside diameter of said front channel.

5. The device of claim 1 in which said body is generally V-shaped in horizontal cross section; said front channel extending along the apex of said V-shaped body.

6. The device of claim 1 in which said body is extruded of opaque material.

* * * * *